United States Patent
Ding et al.

(10) Patent No.: US 6,768,924 B2
(45) Date of Patent: Jul. 27, 2004

(54) METHOD AND APPARATUS FOR CAPTURE VERIFICATION BASED ON PROPAGATED ELECTRICAL ACTIVITY

(75) Inventors: Jiang Ding, Maplewood, MN (US); Yinghong Yu, Maplewood, MN (US); Julio C. Spinelli, Shoreview, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 345 days.

(21) Appl. No.: 10/038,225

(22) Filed: Jan. 3, 2002

(65) Prior Publication Data

US 2003/0125777 A1 Jul. 3, 2003

(51) Int. Cl.[7] .......................... A61N 1/362; A61N 1/368
(52) U.S. Cl. ........................................................ 607/28
(58) Field of Search ................................ 607/9, 27, 28

(56) References Cited

U.S. PATENT DOCUMENTS

| | | | |
|---|---|---|---|
| 5,222,493 A | 6/1993 | Sholder | 607/27 |
| 5,285,780 A | 2/1994 | Tsuji et al. | 607/13 |
| 5,320,643 A | 6/1994 | Roline et al. | 607/28 |
| 5,324,310 A | 6/1994 | Greeninger et al. | 607/28 |
| 5,417,718 A | 5/1995 | Kleks et al. | 607/28 |
| 5,476,486 A * | 12/1995 | Lu et al. | 607/28 |
| 5,476,487 A | 12/1995 | Sholder | 607/28 |
| 5,507,782 A | 4/1996 | Kieval et al. | 607/9 |
| 5,601,615 A | 2/1997 | Markowitz et al. | 607/28 |
| 5,666,958 A | 9/1997 | Rothenberg et al. | 600/509 |
| 5,702,427 A | 12/1997 | Ecker et al. | 607/28 |
| 5,713,934 A | 2/1998 | Leckrone | 607/28 |
| 5,741,309 A | 4/1998 | Maarse | 607/9 |
| 5,855,594 A | 1/1999 | Olive et al. | 607/28 |
| 5,861,012 A | 1/1999 | Stroebel | 607/28 |
| 5,861,013 A | 1/1999 | Peck et al. | 607/28 |
| 5,871,512 A | 2/1999 | Hemming et al. | 607/28 |
| 5,873,898 A | 2/1999 | Hemming et al. | 607/28 |
| 5,954,756 A | 9/1999 | Hemming et al. | 607/28 |
| 6,128,535 A * | 10/2000 | Maarse | 607/28 |
| 6,148,234 A | 11/2000 | Struble | 607/28 |
| 6,615,089 B1 * | 9/2003 | Russie et al. | 700/21 |
| 2001/0049543 A1 * | 12/2001 | Kroll | 607/28 |

* cited by examiner

*Primary Examiner*—Carl Layno
*Assistant Examiner*—B. Webb
(74) *Attorney, Agent, or Firm*—Thomas J. Nikolai; Nikolai & Mersereau, P.A.

(57) ABSTRACT

An implantable cardiac rhythm/function management device that automatically determines whether or not a pacing stimulus to the ventricles results in capture by detecting propagated depolarizations at stimulating and non-stimulating electrodes. The device of the present invention is suitable for use in either a single or multiple electrode pacing/sensing configuration and may be utilized to verify either atrial or ventricular capture of a heart having either normal or abnormal intrinsic AV conduction.

39 Claims, 7 Drawing Sheets

METHOD AND APPARATUS FOR CAPTURE VERIFICATION BASED ON PROPAGATED ELECTRICAL ACTIVITY

BACKGROUND OF THE INVENTION

I. Field of the Invention

The present invention relates generally to the field of cardiac rhythm/function management devices, and more particularly relates to cardiac rhythm/function management devices that automatically determine whether or not a pacing stimulus to the atrium(s) and/or ventricle(s) results in capture. The cardiac device of the present invention is suitable for use in either a unipolar or bipolar pacing/sensing configuration and may be utilized to verify either atrial or ventricular capture in a heart having either normal or abnormal intrinsic conduction.

II. Background of the Prior Art

In a normal heart, the sino-atrial (SA) node initiates the myocardial stimulation of the atrium. The SA node comprises a bundle of unique cells disposed within the roof of the right atrium. The SA node cells are in electrical communication with the surrounding atrial muscle cells such that the depolarization of the SA node cells causes the adjacent atrial muscle cells to depolarize. The depolarization causes the atria to contract forcing blood into the ventricles. The depolarization of the SA node is further communicated to the atrio-ventricular (AV) node. The AV node communicates the depolarization impulse to the ventricles sequentially through the Bundle of His and Purkinje fibers. The time for the depolarization impulse to travel from the AV node through the Bundle of His and Purkinje fibers results in a brief delay for ventricular contraction. Therefore, ventricular contraction or systole lags behind atrial systole. The sequential contraction of the atria and ventricles allows the atria to fill the ventricles before the ventricles pump the blood through the body and lungs. Atrial and ventricular diastole follow wherein the heart muscle or myocardium is re-polarized and relaxed prior to the next contraction.

When the intrinsic stimulation system fails or functions abnormally an implanted pacing device may be needed to deliver an electrical (pacing) stimulus to the heart. When the strength of the stimulus is sufficient, the artificial electrical stimulus can cause the muscle cells surrounding the electrode to depolarize. This depolarization will spread out through the entire chamber or chambers of the heart and result in contractions. Thus, electrical stimulation, when applied at the appropriate time and location, can maintain the proper heart rate and/or efficient contraction. This typically is the purpose of a cardiac rhythm/function management device. Further, certain conditions result in heart fibrillation and require a significant electrical stimulus to defibrillate the heart.

Cardiac rhythm/function management devices are widely used for supplanting the heart's natural pacing functions and for defibrillating the heart. The devices may be used to correct various abnormalities, including total or partial heart block, arrhythmias, myocardial infarctions, congestive heart failure, congenital heart disorders, and various other rhythm disturbances within the heart. A cardiac rhythm/function management device typically includes a pulse generator to generate an electrical stimulus and at least one lead to transfer the electrical stimulus to the heart. The electrical stimulus or pacing stimulus may be directed to one or more of the atria and/or ventricles. Further, the leads may also be used to sense for electrical impulses in one or more of the atria and/or the ventricles. A ventricular lead of the cardiac rhythm/function management device may also be used in a defibrillation mode to defibrillate the heart. The cardiac rhythm/function management device typically includes a pacing output circuit designed to selectively deliver stimulus pulses through the lead to one or more electrodes. The pacing output circuit includes a power supply, switches, a pacing charge storage capacitor, and a coupling capacitor, all of which cooperatively operate under the direction of a controller to perform a charging cycle, a pacing cycle, and a recharging cycle.

Regardless of the particular device's configuration (ie: ventricular pacing, atrial pacing, multi-chamber pacing, etc.), cardiac rhythm/function management devices generally operate by stimulating the muscle cells adjacent to the pacing electrode or set of electrodes. The devices provide one or more particular stimuli to the heart that overcomes the abnormality and/or confers an appropriate rhythm. When the strength of the pacing stimulus meets or exceeds a threshold level, the resulting depolarization propagates through the heart. A pacing stimulus that initiates a propagated depolarization is said to have "captured" the heart.

Thus, the success of a pacing stimulus in capturing the heart depends on whether or not the current of the pacing stimulus to the myocardium exceeds the threshold value. The threshold value, frequently referred to as the capture threshold, is related to the electrical field intensity required to alter the permeability of the myocardial cells to thereby initiate cell depolarization. If the local electrical field associated with the pacing stimulus does not exceed the capture threshold, then the permeability of the myocardial cells will not be altered sufficiently to initiate depolarization. If, on the other hand, the local electrical field associated with the pacing stimulus exceeds the capture threshold, then myocardial cell permeability will be sufficiently altered to propagate depolarization.

The capture threshold may vary over time. Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture.

The ability of a pacing device to detect capture is desirable in that delivering stimulation pulses having energy far in excess of the patient's capture threshold is wasteful of the limited power supply. In order to minimize current drain on the power supply, it is desirable to automatically adjust the device to deliver the lowest energy level that will reliably capture the heart. To accomplish this, a process known as "capture verification" must be performed wherein the device monitors to determine whether an evoked depolarization occurs in the pre-selected heart chamber following the delivery of each pacing stimulus pulse to the chamber.

In many cardiac rhythm/function management devices, the device does not determine whether or not a pacing stimulus or set of stimuli have promoted the heart to contract. Efforts have been made to develop a cardiac rhythm/function management device that verifies capture. For example, special sensing amplifiers and algorithms have been added to the device to detect evoked potential presented in an electrode after a stimulus is delivered to that electrode. However, it has been found that such capture verification is difficult due to polarization voltages or "afterpotential" which develop at the heart tissue/electrode interface following the application of the stimulation pulses.

The ability to verify capture is further affected by other variables, including patient activity, body position, drugs, lead movement, noise, etc. Because of the multiplicity of variables, the algorithms used to determine capture are frequently complex. The complexity adds to the costs and the likelihood of errors in the software. Also, adding specialized components to verify capture increases the cost and complexity of the pacing apparatus. Therefore, a need exists for an apparatus for sensing ventricular capture that does not require specialized components, such as sense amplifiers, to detect ventricular activities. Further, there is a need for an apparatus and method for verifying ventricular capture that does not require sophisticated signal processing.

U.S. Pat. No. 5,222,493 issued to Sholder (the '493 patent) describes a cardiac rhythm management device having a capture verification circuit that senses evoked potential between a pacing electrode and an additional indifferent electrode. Sholder describes positioning the additional indifferent electrode on the front or back of the header of the pacemaker or, alternatively, on an additional lead or an existing pacing lead. Although an indifferent electrode is less affected by saturation voltages, the capture verification circuit described by Sholder requires direct input from the stimulating electrode. Thus, the electrical charges that build up around the stimulating electrode after delivery of a pacing pulse affects the accurate determination of whether the pacing results in capture. Additionally, Sholder does not describe a verification circuit for capture verification of biventricular or other multi-site stimulation modes. Further, the requirement of an indifferent electrode and either a switching circuit or an additional sensing amplifier may increase the costs thereof U.S. Pat. No. 6,148,234 issued to Struble (the '234 patent) describes a cardiac rhythm management system having a form of capture verification. The device described in the '234 patent includes a two electrode, biventricular pacing system that verifies non-capture (from one of the two electrodes) by determining whether there is conducted depolarization on any electrode. The concept is that when one of the two stimulating electrodes captures while the other fails, the depolarization that is induced by the capturing electrode will conduct to the location of the non-capturing electrode and be detected by the latter electrode. Although detection of this "conducted" depolarization from a non-capturing electrode may be easier than detection of an "evoked" depolarization from a capturing electrode, Struble does not describe a device fully operable when an AV block is present, and further does not describe a device having a single electrode mode or three or more electrode mode. Thus, there is a need for an apparatus and method which is less affected by post-stimulation artifacts, more versatile and reliable to verify both capture and non-capture utilizing different stimulation configurations (for example, single or multiple electrode stimulation) wherein various heart conditions are present (for example, normal or abnormal AV conduction).

The present invention meets the above needs and provides additional improvements and advantages that will be recognized by those skilled in the art upon review of the following figures and description.

SUMMARY OF THE INVENTION

The present invention provides a device and method for verifying capture which looks for propagated depolarization originating from heart muscle cells in distant locations that spread or propagate towards a detecting electrode. The device and method of the present invention confirms capture if a propagated depolarization is detected at a non-stimulating electrode and for the same cardiac cycle, no propagated depolarization is detected at any stimulating electrodes shortly after a stimulation. By checking for propagated depolarization from all available electrodes, both stimulating and non-stimulating, the present invention is able to verify capture (or non-capture) with a variety of stimulation configurations (single or multiple electrode) and under various patient conditions (normal or abnormal intrinsic conduction). The present invention does not require special sense amplifiers and complex algorithms, thereby simplifying implementation and reducing costs.

The cardiac electrical stimulation system of the present invention has an autocapture stimulation/sensing configuration for use in the atrium or ventricles and generally includes one or more leads, a pulse generator, a sensing circuit and a control unit. The leads have one or more stimulating electrodes and one or more passive (non-stimulating) electrodes and may be positioned in the atrium or ventricles of the heart. The pulse generator is electrically coupled to the stimulating electrodes for providing an electrical stimulus to at least one of the atrium and ventricles of the heart. The sensing circuit is electrically coupled to the stimulating electrodes and the passive electrodes, wherein the sensing circuit senses a response by the heart to the electrical stimulus.

The sensing circuit includes a timing circuit, a first detection circuit coupled to the stimulating electrodes, and a second detection circuit coupled to the passive electrodes. Capture of the electrical stimulus is confirmed or verified if the second detection circuit detects depolarization but the first detection circuit does not detect depolarization during a predetermined detection interval. Non-capture of the electrical stimulus by the heart is confirmed if the first detection circuit detects depolarization during the predetermined detection window or no depolarization is detected by either detection circuit during the predetermined detection window.

In use, after the leads, having the stimulating and passive electrodes, are in the desired position within the heart, the pulse generator delivers an electrical stimulus to one or more stimulating electrode(s). The system then senses for depolarization at both the stimulating and passive electrodes during the predetermined detection window. The timing interval of the predetermined detection window may be adjusted to exclude sensing of stimulus artifacts. If capture of the electrical stimulus by the heart is not confirmed, the amplitude of the electrical stimulus may be increased.

The control unit configures the electrodes by designating them as stimulation or passive, controls the delivery of stimuli, determines the detection window, coordinates the execution of capturation verification, and changes amplitude of the stimulus according to the results of capture verification.

These and other advantages of the present invention will become readily apparent to those skilled in the art from a review of the following detailed description of the preferred embodiment especially when considered in conjunction with the claims and accompanying drawings in which like numerals in the several views refer to corresponding parts.

DETAILED DESCRIPTION OF THE INVENTION

The present invention represents broadly applicable improvements to cardiac rhythm/function management systems capable of capture verification. The embodiments detailed herein are intended to be taken as representative or exemplary of those in which the improvements of the invention may be incorporated and are not intended to be limiting. For purposes of discussion, and without any limitation intended, the capture verification will be described in conjunction with particular lead configurations and algorithms. Those skilled in the art will appreciate that a variety of other lead configurations and algorithms may utilize the capture verification of the present invention.

Figure 1:
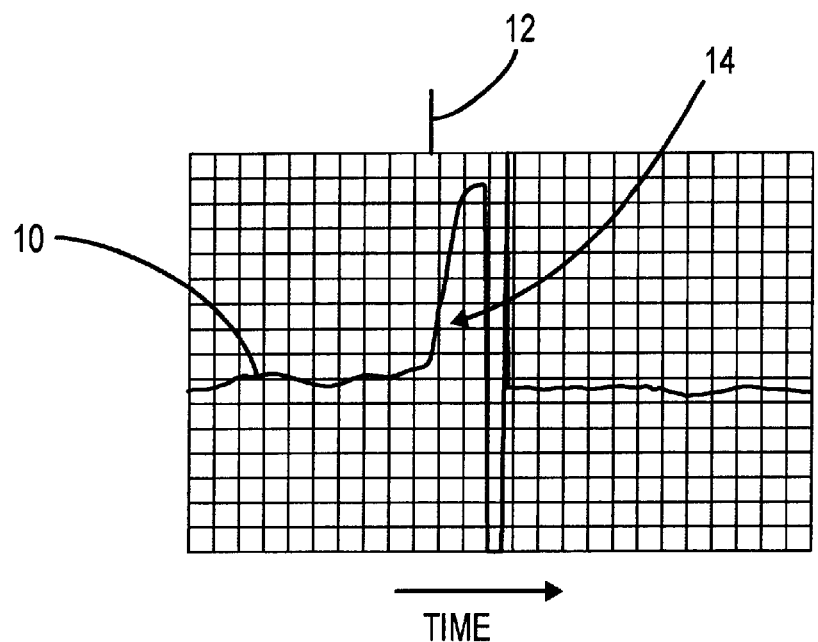
FIG. 1 shows a graph of an electrogram signal wherein a pacing stimulus has captured the ventricle.

FIG. 1 shows a graph or trace of a recorded electrical signal 10 detected from a stimulating electrode placed in a ventricle. The graph shows the electrical signals detected both before and after delivery of an electrical stimulus represented by marker 12. The electrical stimulus 12 of FIG. 1 captures the heart. A depolarization or evoked potential originates near the tip of the stimulating electrode shortly after delivery of the electrical stimulus 12. As seen in FIG. 1, the evoked potential is completely embedded in the stimulus artifact 14 which has a much larger amplitude than the evoked potential and, thus, the evoked potential is not typically detected without use of a special amplifier and algorithm. Typically, after delivery of an electrical stimulus 12, the muscle cells around the electrode are in a non-excitatory state (i.e. refractory period), during which the cells will not be depolarized again for a certain period of time. As a result, there is no depolarization signal detected later in time, after the resulting stimulus artifact 14.

Figure 2:
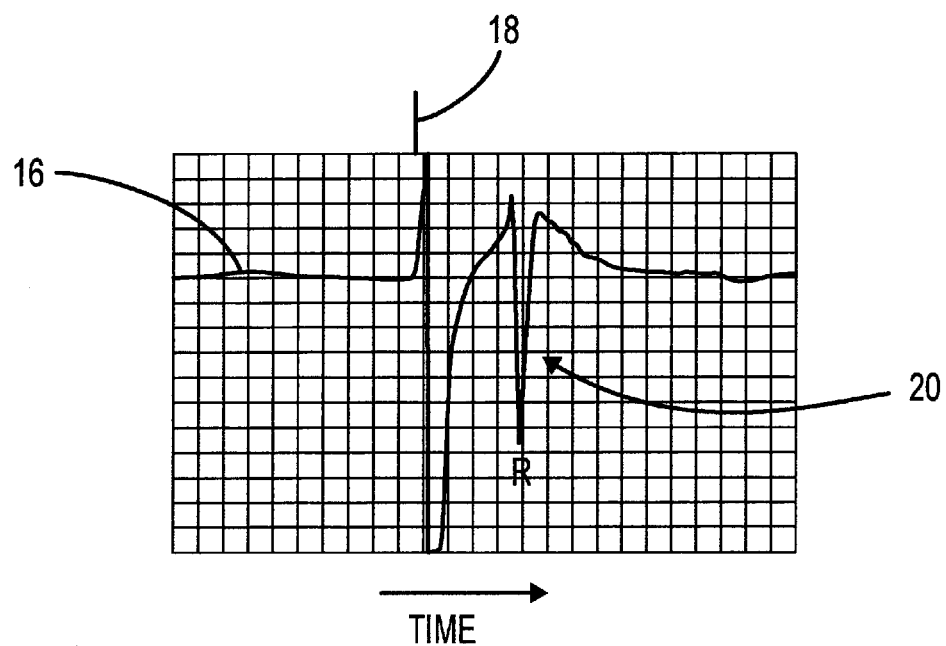
FIG. 2 shows a graph of an electrogram signal wherein the pacing stimulus has failed to capture the ventricle.

FIG. 2 shows a graph or trace of a recorded electrical signal 16 detected from a stimulating electrode placed in a ventricle. The graph shows the signal 16 detected both before and after delivery of an electrical stimulus represented by marker 18. The delivered electrical stimulus is shown to be ineffective, resulting in non-capture. However, because the heart's muscle cells around the stimulation electrode are still excitatory after delivery of the stimulus, any depolarization originating elsewhere and propagating towards the electrode depolarizes the muscle cells around the electrode. The propagated depolarization is detected at the stimulation electrode as a QRS complex 20. Thus, capture verification of the present invention is performed by determining whether or not there is a propagated depolarization signal detected at a stimulating electrode. Adding the detection of a propagated depolarization at a passive electrode is for the purpose of capture verification in the scenario of complete heart block where there is little or no spontaneous cardiac depolarizations. In this case, capture can be confirmed if and only if there is a propagated depolarization detected at the passive electrode, but no such depolarizations are detected at any stimulating electrodes.

Figure 3:
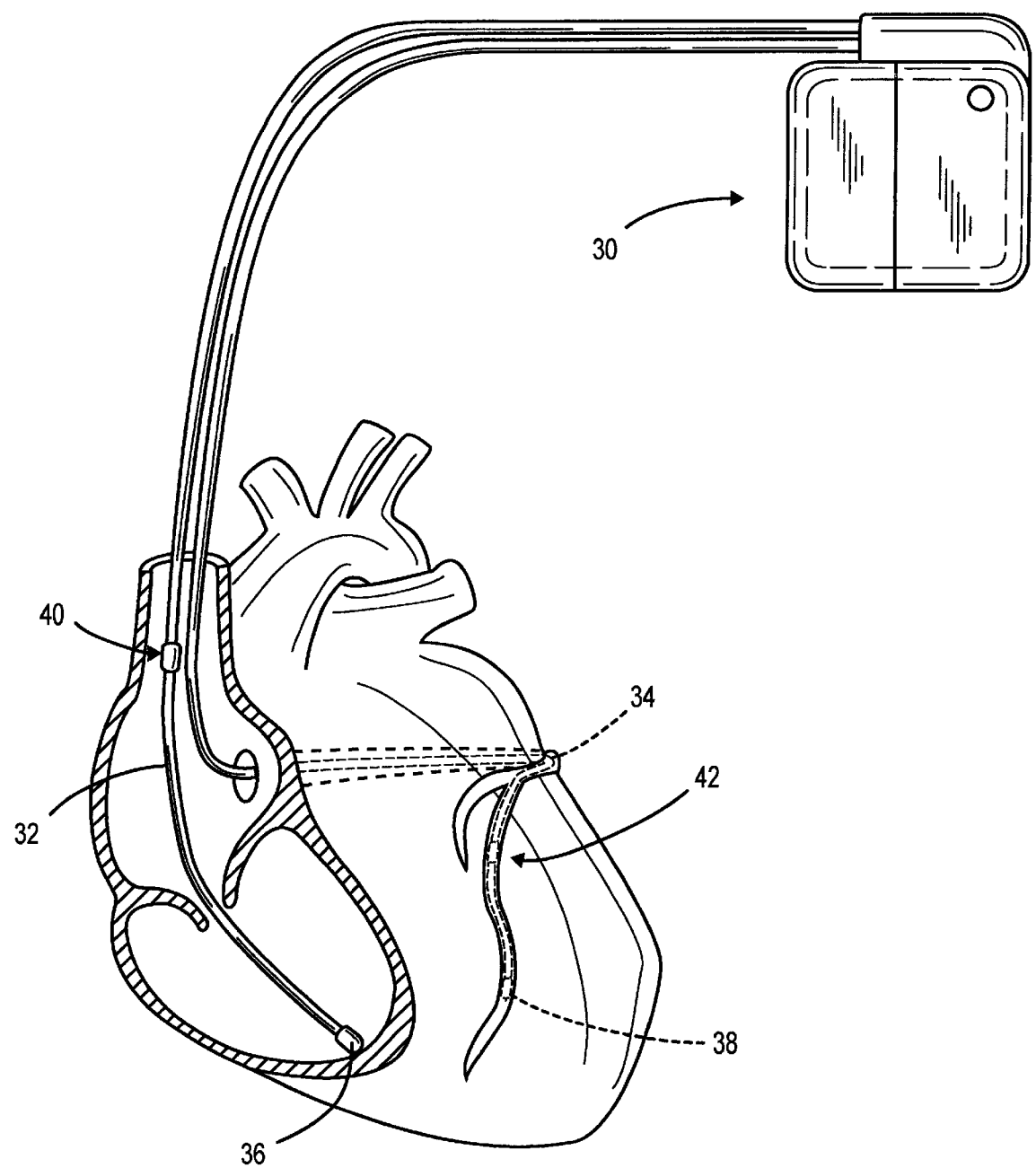
FIG. 3 is a partial sectional perspective view of a cardiac rhythm/function management system, showing a ventricular lead and epicardial lead coupled thereto.

FIG. 3 illustrates a cardiac rhythm/function management (CRFM) system 30 electrically coupled to a right ventricular lead 32 and an epicardial left ventricular lead 34. The right ventricular lead 32 includes at least one sensing/pacing electrode 36 for stimulating the right ventricle and may further include electrodes 40 suitable for use in pacing/sensing the right atrium. The epicardial lead 34 may include at least one pacing/sensing electrode 38 for stimulating the left ventricle and may further include electrode 42 configured as passive electrode. The CRFM system 30 typically includes a stimulation and a sensing circuit for each electrode, a pulse generator, a timing circuit, and a control logic unit. The method and apparatus of the CRFM system that are specific to this invention will be discussed below in greater detail. Those skilled in the art will appreciate that the CRFM system 30 may further include an external programmer and telemetering circuit to telemeter status information, including stimulation mode and other parameters, to the external programmer and to receive controlling signals from the external programmer (not shown).

Figure 4:
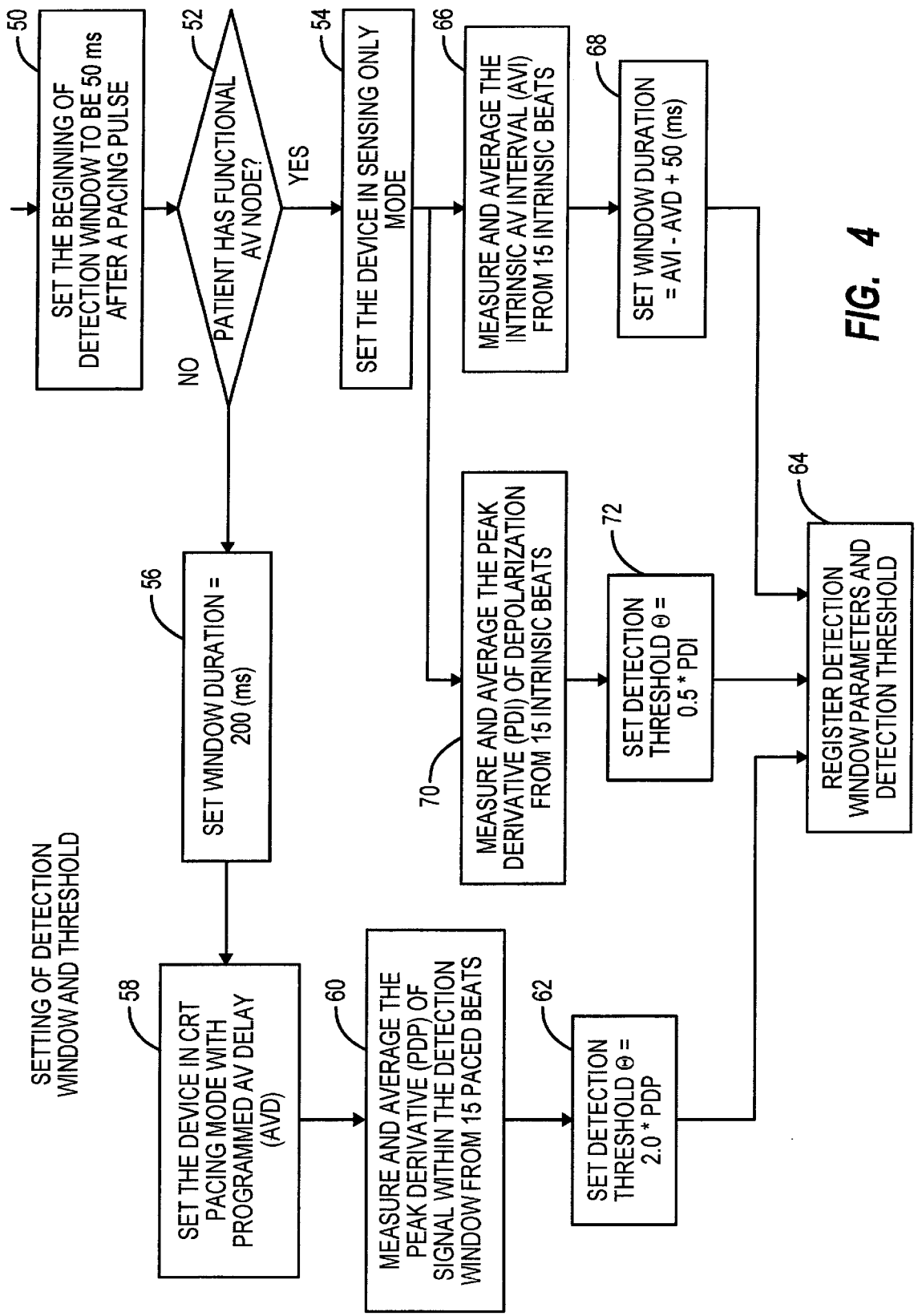
FIG. 4 is a block diagram showing an embodiment of a method of setting the detection window and threshold in accordance with the present invention.

With reference now to FIG. 4, and without any limitation intended, the preferred method of setting the detection window and detection threshold of the present invention will next be described. First, the start of the detection window is set to commence a preset time after an electrical stimulus is delivered. In the preferred embodiment, when pacing, the detection window is set to start 50 msec. after a pacing pulse is delivered (see block 50). If the patient's heart does not have a functional AV node (see decision block 52), then the detection window is set to a predetermined duration, for example, without limitation, 200 msec. (see block 56). When the AV node is non-functional and the duration of the detection window has been set, the device is set in a particular CRT stimulation mode, for example, bi-ventricular pacing with a programmed AV delay (see block 58). The peak derivative from pacing (PDP) of the signal detected during the detection window may be measured and averaged over a period of 15 pacing cycles, for example. (See Block 60.) The detection threshold is then set equal to an amount greater than the average PDP, for example, two times greater than the average PDP (see block 62). The detection window (in this case a predetermined duration) and detection threshold parameters are then stored in memory of the device (see block 64).

When the AV node is functional, the CRFM system is set for "sensing only" mode (see block 54). Then, intrinsic AV interval (AVI) is measured and averaged over the same 15 intrinsic beats (see block 66). Without limitation, the detection window duration is then set equal to the average intrinsic AV interval plus 50 msec. minus the programmed AV delay (see block 68). Also, the peak derivative of intrinsic depolarization (PDI) of the signal detected during the detection window is measured and averaged over 15 intrinsic beats, for example (see Block 70). The detection threshold is then set, for example, equal to half the average peak PDI (see block 72). The detection window and detection threshold parameters are then stored in memory of the stimulation device (see block 64).

Figure 5:
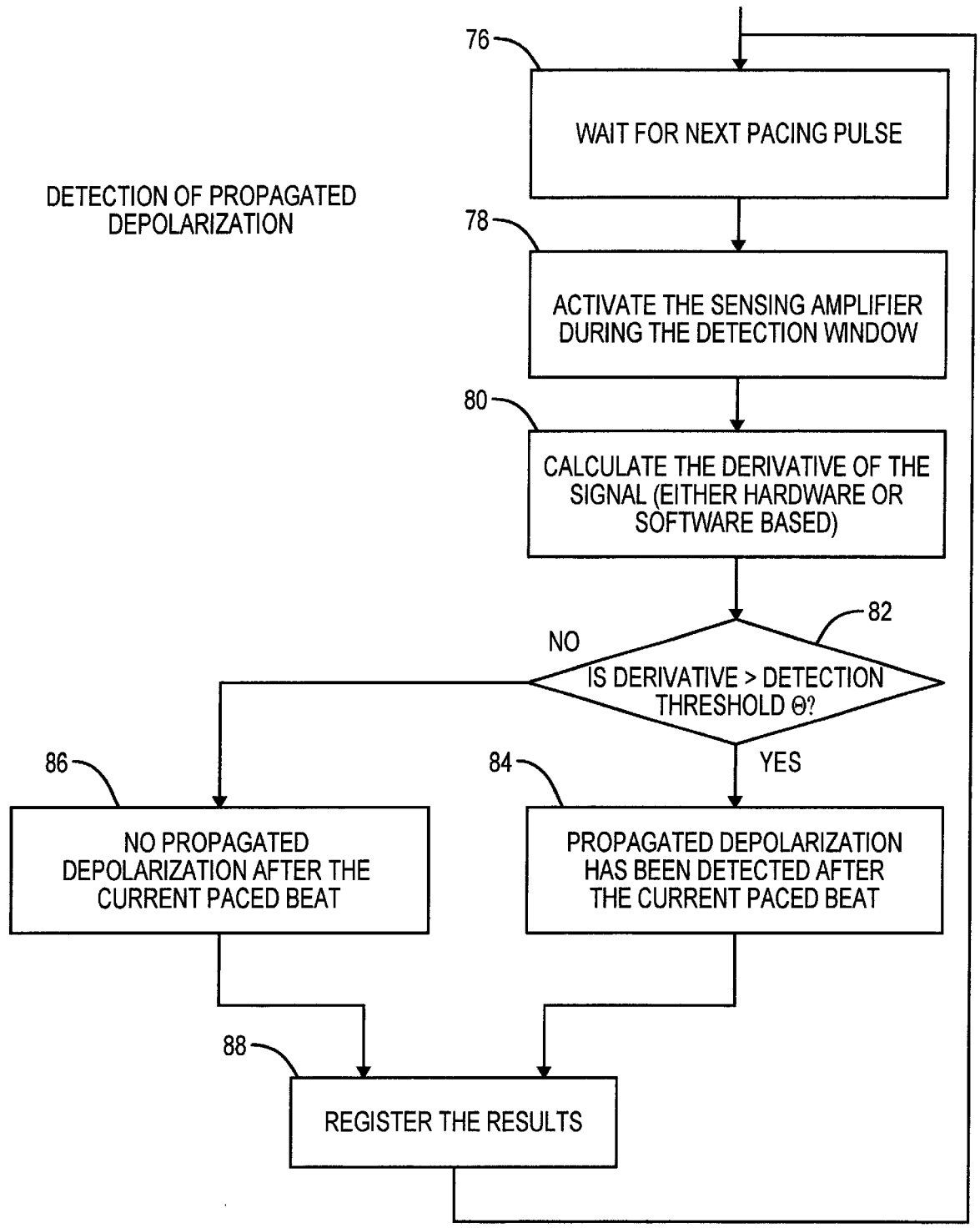
FIG. 5 is a block diagram showing an embodiment of a method of detecting propagated depolarization in accordance with the present invention.

FIG. 5 illustrates the preferred method of detecting propagated depolarization. Once the detection window and detection threshold are set, the device waits until the next electrical stimulus. For example, a pacing pulse may be delivered (see bloc 76) and then a sense amplifier is activated during the detection window (see block 78). The derivative of the sensed signal from the sense amplifier is then determined utilizing known hardware or software coupled to the device (see block 80). The detection circuit of the device then determines whether the derivative of the sensed signal is greater than the detection threshold (see decision block 82). If the derivative is greater than the detection threshold, then detection of a propagated depolarization after the corresponding electrical stimulus is assumed (see block 84). If the derivative is less than or equal to the detection threshold, then the presence of no propagated depolarization after the corresponding electrical stimulus is assumed (see block 86). The results of the detection determination are then stored in memory of the stimulation device (see block 88).

Figure 6:
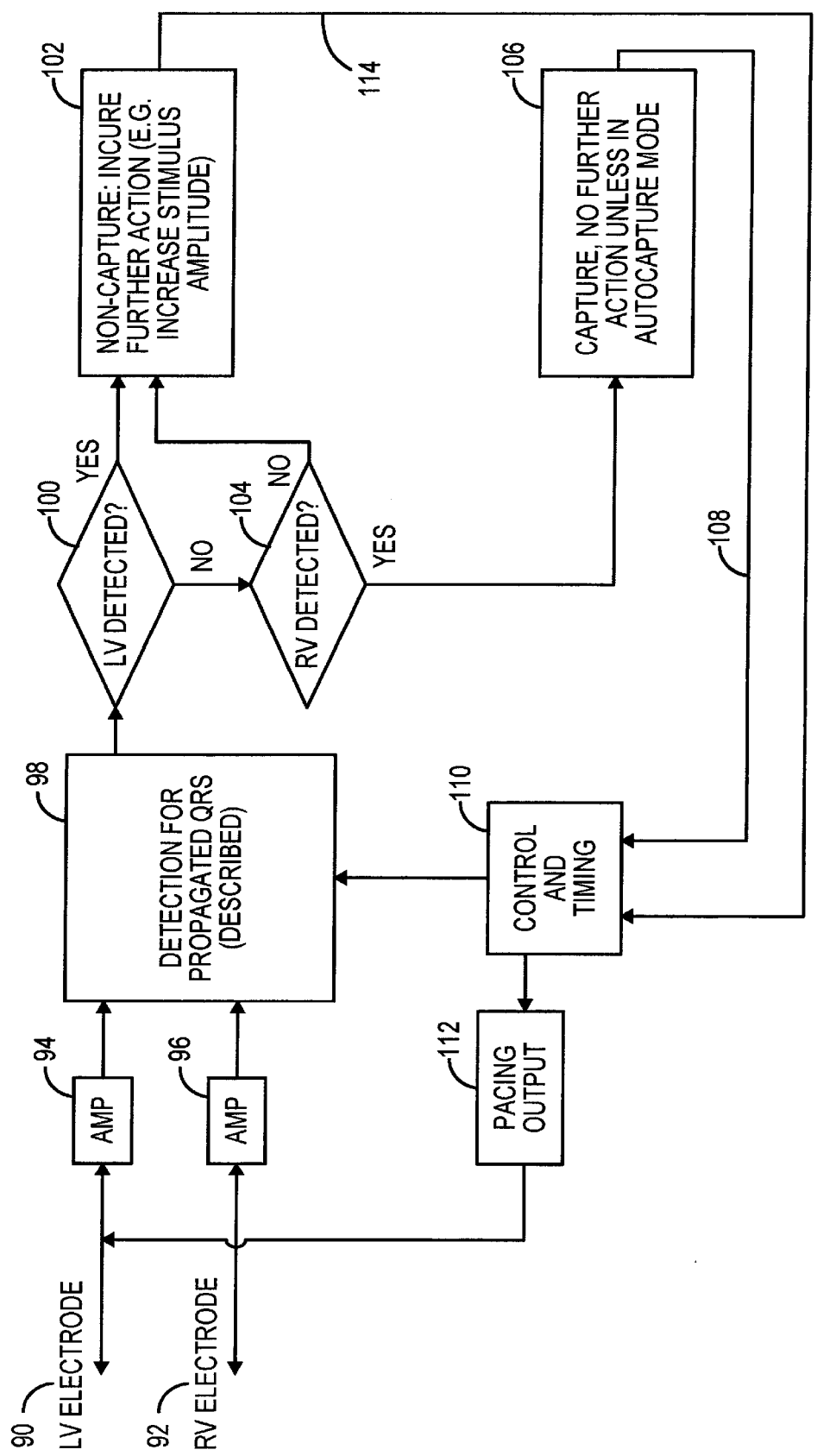
FIG. 6 is a block diagram showing an embodiment of a method of capture verification in accordance with the present invention.

FIG. 6 shows one embodiment of capture detection algorithm of the present invention suitable for use when pacing in the left ventricle and utilizing a right ventricle electrode as a passive or indifferent electrode. The CRFM device is shown electrically coupled to a left ventricular (LV) electrode 90 for pacing and sensing and a right ventricular (RV) electrode 92 for sensing only. The LV electrode 90 and RV electrode 92 are connected to corresponding LV sense amplifier 94 and RV sense amplifier 96. The sense amplifiers amplify the signals indicative of cardiac electrical activity sensed by the corresponding LV electrode 90 and RV electrode 92. The signals from LV sense amplifier 94 and RV sense amplifier 96 are analyzed by one or more detection circuits 98. Those skilled in the art will appreciate that when one detection circuit is utilized to detect propagated depolarization from both the LV electrode 90 and RV electrode 92, then switching and/or memory of known suitable construction may have to be incorporated into the detection circuit. The detection circuit 98 analyzes the signals and determines whether or not a propagated depolarization signal is present at the LV and RV electrodes 90 and 92 during the detection window after an electrical stimulus is delivered. The propagated depolarization detection circuit 98 may identify a propagated depolarization using a variety of methods, including a method based on derivatives (described above with respect to FIGS. 3 and 4), template matching or signal amplitude. The results from the detection circuit are then further analyzed.

If a propagated depolarization is detected from the LV electrode 90, then it is assumed that the electrical stimulus, for example, a pacing pulse, was not capturing the left ventricle (see decision block 100) and the amplitude of the electrical stimulus is increased (see block 102) and pacing continues (see loop 114 and blocks 110 and 112). Likewise, if no propagated depolarization is detected at either the LV electrode or the RV electrode (see decision blocks 100 and 104), then it is assumed that the electrical stimulus was not capturing the left ventricle, and the amplitude of the electrical stimulus is increased (see block 102), and pacing continues (see loop 114 and blocks 110 and 112). If no propagated depolarization is detected at the LV electrode 90, but a propagated depolarization is detected at the RV electrode 92, then capture of the left ventricle by the electrical stimulus is assumed (see block 106), and pacing continues unless the device is in an autocapture mode (see loop 108 and blocks 110 and 112), in which the amplitude of the electrical stimulus may be decreased.

Figure 7:
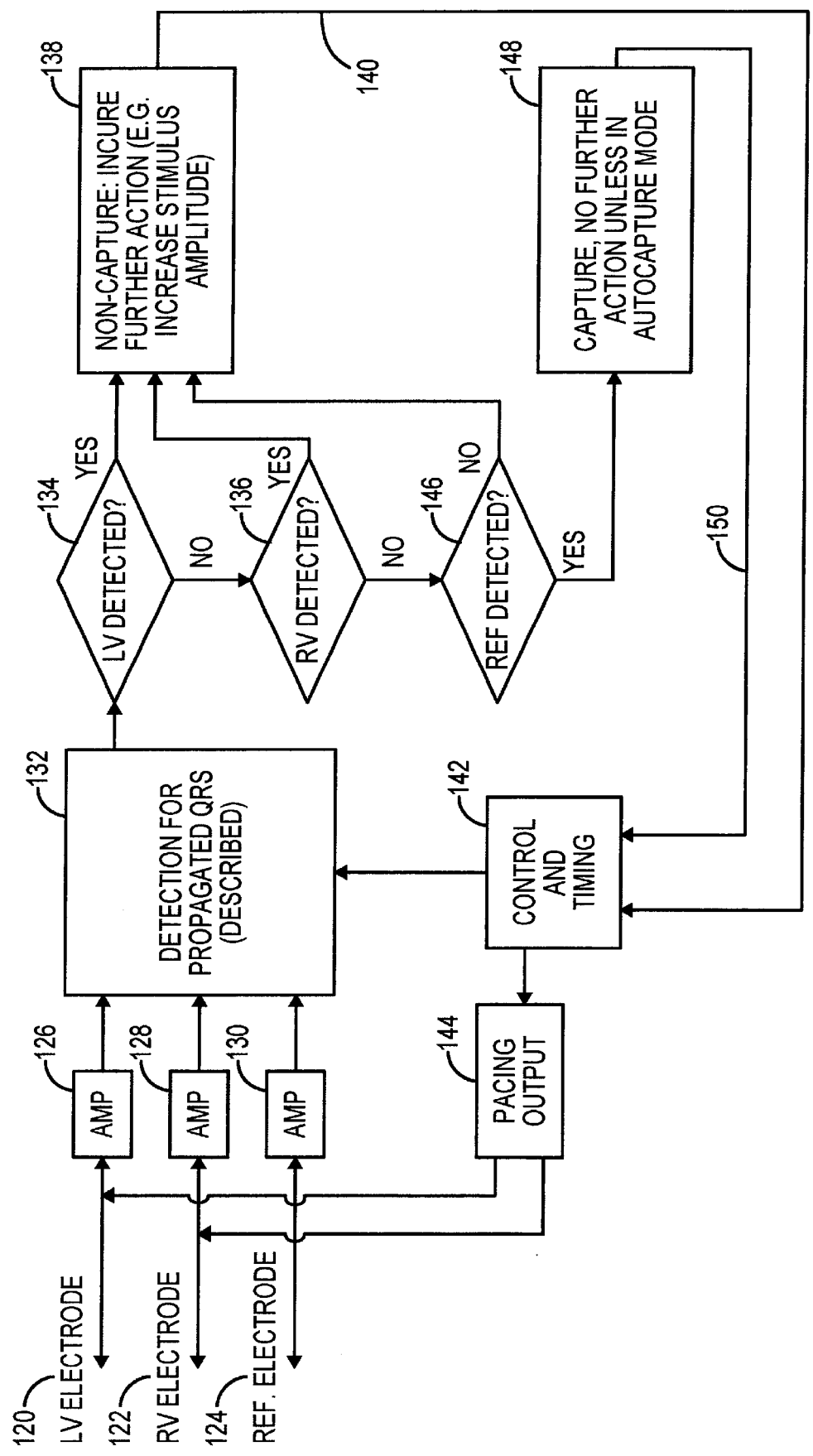
FIG. 7 is a block diagram showing another embodiment of a method of capture verification in accordance with the present invention.

FIG. 7 shows another embodiment of capture detection of the present invention, wherein the embodiment is suitable for use when bi-ventricular pacing in both the left ventricle and right ventricle. It utilizes a reference electrode as a passive or indifferent electrode. Without any limitation intended, the reference electrode may be, for example, a separate electrode of the left or right ventricular lead or a defibrillation electrode of the right ventricular lead. When the electrical stimulus delivered to the left and right ventricle captures the heart, there will be no propagated depolarization detected at either the left or right ventricle electrode. If only one electrode captures the corresponding ventricle by delivering an electrical stimulus, then a propagated depolarization will be detected by the other electrode and non-capture is assumed.

In the case where the heart has an atrio-ventricular conduction block, if the electrical stimulus is not capturing either ventricle, no propagated depolarization may be present and capture may be falsely assumed. In order to overcome this situation, an additional reference electrode may be utilized. If a depolarization is detected at the reference electrode but not at either stimulating electrode (LV or RV), then the depolarization is a propagated depolarization resulting from the stimulation of the two electrodes and, thus, the electrical stimulus is capturing the heart. On the other hand, if no propagated depolarization is detected from any of the three electrodes, then it can be assumed that the electrical stimulus has not captured. Hence, use of an additional electrode, in the case of bi-ventricular pacing, enables the device to verify capture or non-capture independent of whether the patient has functional AV conduction or complete AV block.

With reference again to FIG. 7, the stimulation device is shown electrically coupled to a left ventricular (LV) electrode 120 for pacing and sensing, a right ventricular (RV) electrode 122 for pacing and sensing, and a reference electrode 124 for sensing only. The LV electrode 120, RV electrode 122, and reference electrode 124 are connected to corresponding LV sense amplifier 126, RV sense amplifier 128, and reference sense amplifier 130. The sense amplifiers amplify the signals indicative of cardiac electrical activity sensed by the corresponding electrodes. The signals from LV sense amplifier 126, RV sense amplifier 128, and reference sense amplifier 130 are analyzed by one or more detection circuits 132. As described above, when one detection circuit is utilized to detect propagated depolarization from the LV electrode 120, RV electrode 122, and reference electrode 124, then additional switching and/or memory of known suitable construction may need to be incorporated into the detection circuit 132.

The detection circuit 132 analyzes the signals and determines whether or not a propagated depolarization signal is present at the LV, RV and reference electrodes 120–124 during the detection window after an electrical stimulus is delivered. As noted above, the propagated depolarization detection circuit 132 may identify a propagated depolarization using a variety of methods, including a method based on derivatives (described above with respect to FIGS. 3 and 4), template matching or signal amplitude. The results from the detection circuit are then further analyzed.

If a propagated depolarization is detected from the LV electrode 120 or RV electrode 122, then it is assumed that the electrical stimulus, for example, a pacing pulse, was not capturing one of the ventricles (see decision blocks 134 and 136), the amplitude of the electrical stimulus is increased (see block 138) and pacing continues (see loop 140 and blocks 142 and 144). Likewise, if no propagated depolarization is detected at the LV electrode 120, RV electrode 122, or the reference electrode 124 (see decision blocks 134, 136, and 146), then it is assumed that the electrical stimulus, was not capturing the ventricles, and the amplitude of the electrical stimulus is increased (see block 138), and pacing continues (see loop 140 and blocks 142 and 144). If no propagated depolarization is detected at the LV electrode 120 or the RV electrode 122, but a propagated depolarization is detected at the reference electrode 124, then capture of the ventricles by the electrical stimulus is assumed (see block 148) and pacing continues unless the device is in an autocapture mode (see loop 150 and blocks 142 and 144), in which the amplitude of the stimulus may be decreased.

Figure 8:
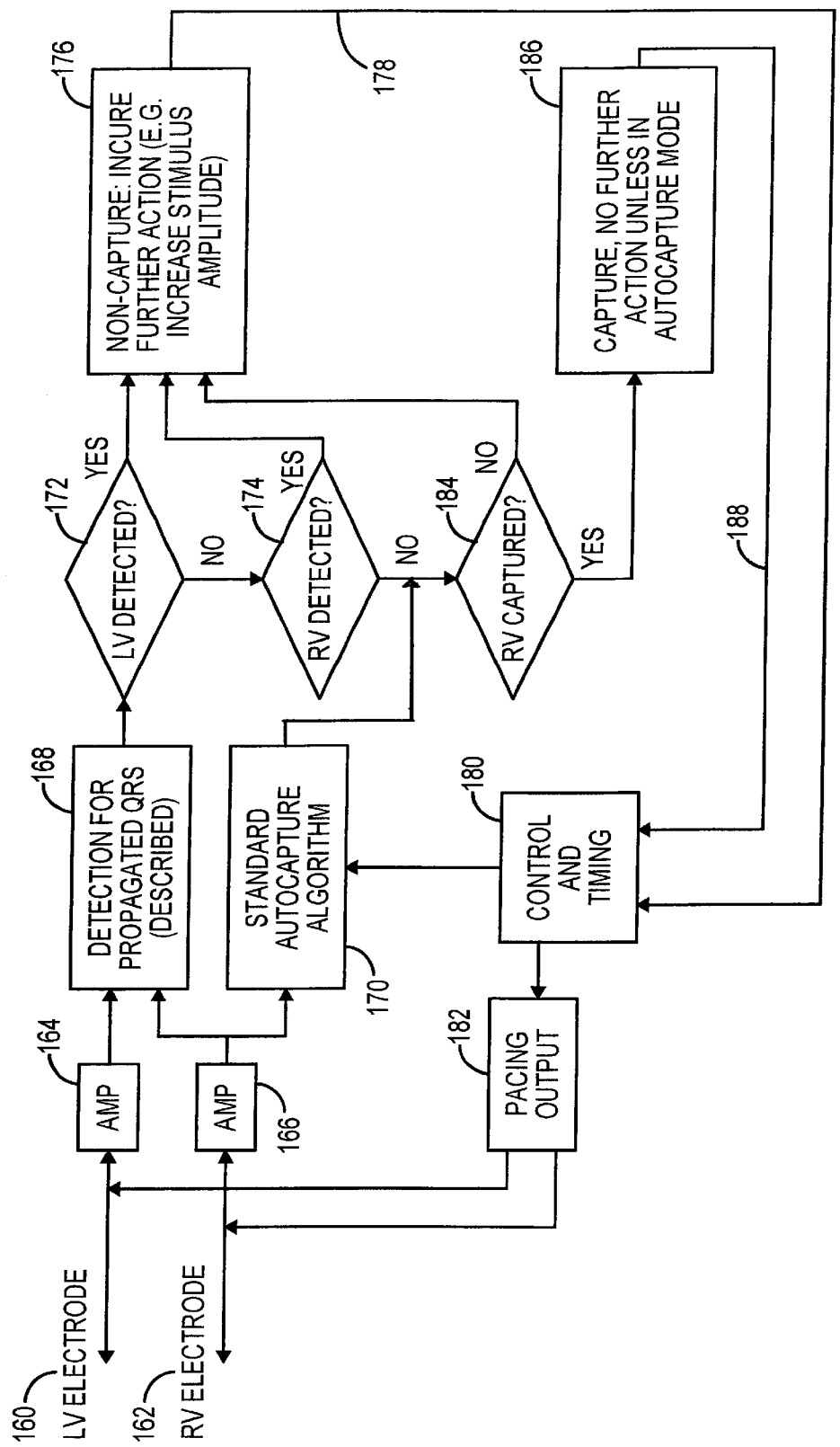
FIG. 8 is a block diagram showing still another embodiment of a method of capture verification in accordance with the present invention.

FIG. 8 shows yet another algorithm for capture detection in accordance with the present invention, wherein the embodiment is suitable for use when pacing in both the left and right ventricle without utilizing a third reference electrode. As described above, when electrical stimulus delivered to the left and right ventricle captures the heart, there will be no propagated depolarization detected at either the left or right ventricle electrode. If only one ventricle is captured by the electrical stimulus from the corresponding electrode, then a depolarization will be detected by the other electrode and non-capture is assumed.

In the case of an atrial-ventricular conduction block, if no propagated depolarization is detected at either the LV or RV electrode, then an autocapture circuit of known suitable design may be utilized to detect evoked potential from the RV stimulating electrode. Such evoked potential is only present after an effective (i.e. capturing) stimulation and is detected by amplifiers in the autocapture circuit. An ineffective biventricular stimulation will not cause an evoked potential to be detected by the autocapture circuit. Without limitation, in the preferred embodiment the autocapture circuit may be of the type disclosed in U.S. Pat. Nos. 6,169,921, 6,192,275, 6,226,551, U.S. patent application Ser. No. 09/753,738 for "Autocapture Pacing/Sensing Configuration" filed Jan. 2, 2001, and U.S. patent application Ser. No. 09/206,329 for "Autocapture Pacing/Sensing Configuration" filed Dec. 12, 1998.

The algorithm for capture detection shown in FIG. 8 includes a left ventricular (LV) electrode 160 for pacing and sensing, and a right ventricular (RV) electrode 122 for pacing and sensing. The LV electrode 160 and RV electrode 162 are connected to corresponding LV sense amplifier 164 and RV sense amplifier 166. The sense amplifiers amplify the signals indicative of cardiac electrical activity sensed by the corresponding electrodes. The signals from LV sense amplifier 164 are analyzed by detection circuits 168 similar to those above described detection circuits, while the signals from the RV sense amplifier are analyzed by both the detection circuit 168 and an autocapture circuit 170 (that detects evoked potential sensed at the RV electrode 162).

The detection circuit 168 analyzes the signals and determines whether or not a propagated depolarization signal is present at the LV and RV electrodes 160 and 162 during the detection window after an electrical stimulus is delivered. The results from the detection circuit are then further analyzed. If a propagated depolarization is detected from the LV electrode 160 or RV electrode 162, then it is assumed that the electrical stimulus, for example, a pacing pulse, was not capturing one of the ventricles (see decision blocks 172 and 174), and the amplitude of the electrical stimulus is increased to better guarantee capture (see block 176) and pacing continues (see loop 178 and blocks 180 and 182). Likewise, if no propagated depolarization is detected at the LV electrode 120 and RV electrode 122 (see decision blocks 172 and 174) and the autocapture circuit 170 does not detect an evoked potential at the RV electrode 162, then it is assumed that the electrical stimulus was not capturing the ventricles (see decision block 184), and the amplitude of the electrical stimulus is again increased (see block 176), and pacing continues (see loop 178 and blocks 180 and 182). If no depolarization is detected at the LV electrode 160 or the RV electrode 162, but capture at the RV electrode 162 is verified by the autocapture circuit 170, then capture of the ventricles by the electrical stimulus is assumed (see block 186) and pacing continues unless the device is in an autocapture mode (see loop 188 and blocks 180 and 182), where the amplitude of the stimulus may be decreased by a small increment in an attempt to conserve current drain from a battery power source.

Of course, for each of the above described embodiments, those skilled in the art will appreciate that the depolarization detection circuit and autocapture circuit may be implemented in firmware or software. Also, those skilled in the art will readily recognize variations to the CRFM device to verify capture in any heart chamber and to detect propagated depolarization in any heart chamber without departing from the scope of the present invention.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A cardiac electrical stimulation system having a capture verification configuration for use in the ventricles, said cardiac electrical stimulation system being configured to include:

at least one stimulating electrode;

at least one passive electrode;

a pulse generator electrically coupled to said stimulating electrodes for providing an electrical stimulus to at least one ventricle of a heart; and a sensing circuit electrically coupled to said at least one stimulating electrode and said at least one passive electrode, said sensing circuit sensing a response by the heart to the electrical stimulus, said sensing circuit including a timing circuit, a detection circuit coupled to said at least one stimulating electrode and said at least one passive electrode, wherein a capture of the heart by the electrical stimulus is confirmed if depolarization is detected at said at least one passive electrode but no depolarization is detected at said at least one stimulating electrode during a predetermined detection interval and non-capture is confirmed if depolarization is detected at said at least one stimulating electrode, or no depolarization is detected at said at least one stimulating electrode and said at least one passive electrode during the said pre-determined detection interval, said detection circuit adapted to detect propagated depolarization resulting from the electrical stimulus during the predetermined detection interval and comprising a detection unit adapted to be enabled during a predetermined detection time window and capable of producing an output proportioned to the derivative of signals sensed by the sensing circuit, following the application of the pacing stimulus to the heart; a comparator for determining whether the output of the detection unit exceeds a predetermined threshold with said comparator confirming detection of propagated depolarization when the output of the detection unit exceeds said predetermined threshold.

2. The stimulation system as recited in claim 1, wherein an amplitude of the electrical stimulus is increased if capture of the heart by the electrical stimulus is not confirmed.

3. The stimulation system as recited in claim 1 wherein the detection circuit establishes the detection time window whose start begins a predetermined time following generation of the pacing stimulus by the pulse generator.

4. The stimulation system as recited in claim 3, wherein the predetermined time following generation of the pacing stimulus is about 50 ms.

5. The stimulation system of claim 3 wherein the duration of the detection time window is about 200 ms in patients with a non-functioning AV node.

6. The stimulation system of claim 3 wherein the duration of the detection time window is a function of a patient's intrinsic AV delay for patients having a functioning AV node.

7. The stimulation system of claim 6 wherein the detection time window duration is set to equal an average of a patient's intrinsic AV delay over a predetermined number of intrinsic beats less an AV delay pre-programmed into the stimulation system plus a predetermined time value.

8. The stimulation system of claim 1 wherein said predetermined threshold is a fraction of an average of a peak derivative of intrinsic depolarizations measured over a predetermined number of intrinsic heart beats for patients having a functioning AV node.

9. The stimulation system of claim 1 wherein said predetermined threshold is a proportion of an average of measured derivative of stimulation-induced electrical signal waveform within the detection time window over a predetermined number of stimulated heart beats for patients with a non-functioning AV node.

10. A cardiac electrical stimulation system having a capture verification configuration for use in the ventricles, said cardiac electrical stimulation system including:
   a left ventricular electrode;
   a right ventricular electrode;
   stimulating means for delivering electrical stimulus to said left ventricular electrode; and
   sensing means electrically coupled to said left and right ventricular electrodes, said sensing means for sensing a response by the heart to electrical stimulus generated by said stimulating means, said sensing means further including a timing circuit, and a detection circuit coupled to said left and right ventricular electrodes, wherein a capture of the heart by the electrical stimulus is confirmed if the detection circuit detects depolarization at said right ventricular electrode but does not detect depolarization at said left ventricular electrode during a predetermined detection interval, and non-capture is confirmed if depolarization is detected at said left ventricular electrode, or no depolarization is detected at any of said left and right ventricular electrodes during the predetermined detection interval, said predetermined detection interval beginning a predetermined time following said delivery of an electrical stimulus to said left ventricular electrode and whose duration is a function of a patient's intrinsic AV delay for patients having a functioning AV node.

11. The stimulation system of claim 10 wherein the predetermined time following said delivery of an electrical stimulus is about 50 ms.

12. The stimulation system of claim 10 wherein the duration of the predetermined detection interval is about 200 ms. for patients having a non-functioning AV node.

13. The stimulation system of claim 10 wherein the duration of the detection interval is set to equal an average of a patient's intrinsic AV delay over a predetermined number of intrinsic beats less an AV delay pre-programmed into the stimulation system plus a predetermined time value.

14. The stimulation system as recited in claim 10, wherein an amplitude of the electrical stimulus is increased if capture of the heart by the electrical stimulus is not confirmed.

15. The stimulation system as recited in claim 10, wherein the predetermined detection interval is set to exclude detection of stimulus artifact.

16. The stimulation system as recited in claim 10, further including a passive electrode, wherein electrical stimulus is delivered to said right ventricular electrode approximately simultaneously with delivery of electrical stimulus to said left ventricular electrode, and further wherein a capture of the heart by the electrical stimulus is confirmed if the detection circuit detects depolarization at said passive electrode but does not detect depolarization at said left and right ventricular electrodes during the predetermined detection interval, and a non-capture is confirmed if depolarization is detected at either of said right and left ventricular electrode or no depolarization is detected at both of said right and left ventricular electrodes and said passive electrode during the predetermined detection interval.

17. The stimulation system as recited in claim 16 wherein an amplitude of the electrical stimulus is increased if capture of the heart by the electrical stimulus is not confirmed.

18. The stimulation system of claim 16 wherein the predetermined detection interval begins a predetermined time following said delivery of an electrical stimulus to the left ventricular electrode and the right ventricular electrode and whose duration is dependent upon whether the patient has a functioning AV node.

19. The stimulation system of claim 18 wherein the predetermined time following delivery of an electrical stimulus is about 50 ms.

20. The stimulation system of claim 18 wherein the duration of the predetermined detection interval is about 200 ms. for patients having a non-functioning AV node.

21. The stimulation system of claim 18 wherein the duration of the detection interval is a function of a patient's intrinsic AV delay for patients having a functioning node.

22. The stimulation system of claim 21 wherein the duration of the detection interval is set to equal an average of a patient's intrinsic AV delay over a predetermined number of intrinsic beats less an AV delay pre-programmed into the stimulation system plus a predetermined time value.

23. A cardiac electrical stimulation system having a stimulation/sensing configuration for use in the ventricles, said cardiac electrical stimulation system including:
   stimulating electrodes;
   a pulse generator electrically coupled to said stimulating electrodes for providing an electrical stimulus to at least one ventricle of a heart; and
   a sensing circuit electrically coupled to said stimulating electrodes, said sensing circuit sensing a response by the heart to the electrical stimulus, said sensing circuit including a timing circuit, and a detection circuit coupled to said stimulating electrodes, said detection circuit including thresholding means for providing an indication when the depolarization is of a predetermined strength.

24. The stimulation system of claim 23 wherein the predetermined strength is a function of an average of a derivative of electrogram signals during the predetermined detection interval over a predetermined number of paced beats for patients having a non-functioning AV node.

25. The stimulation system of claim 23 wherein the predetermined strength is a function of an average of peak derivative signals of intrinsic depolarizations over a predetermined number of intrinsic beats for patients having a functioning AV node.

26. The stimulation system as recited in claim 23, further including a non-stimulating reference electrode wherein capture is confirmed if no depolarization is detected at said stimulating electrodes and a depolarization is detected at said non-stimulating reference electrode during a predetermined detection interval, and non-capture is confirmed if depolarization is detected at any of said stimulating electrode or no depolarization is detected at said non-stimulating reference electrode during the predetermined detections interval.

27. The stimulation system as recited in claim 23, further including an autocapture circuit coupled to one of said stimulating electrodes, wherein said autocapture circuit detects evoked potential after delivery of a stimulus, and further wherein capture of the electrical stimulus is confirmed if no depolarization is detected at said stimulating electrodes during a predetermined detection interval and an evoked potential is detected by said autocapture circuit, and non-capture is confirmed if depolarization is detected at any of said stimulating electrode during the predetermined detection interval or said autocapture circuit does not detect an evoked potential.

28. The stimulation system as recited in claim 27, wherein an amplitude of the electrical stimulus is increased if capture of the heart by the electrical stimulus is not confirmed.

29. The stimulation system as recited in claim 27, wherein the predetermined detection interval is set to exclude detection of stimulus artifacts.

30. The stimulation system of claim 27 wherein the detection interval is set at a fixed value in patients having a non-functioning AV node.

31. The stimulation system of claim 27 wherein the detection interval is a function of a difference between an average of the patient's AV interval over a predetermined number of intrinsic beats and an AV delay value programmed into the stimulation system in patients having a functioning AV node.

32. A method of verifying capture of a patient's heart by an electrical stimulus delivered to at least one ventricle of the heart, said method including the steps of:
  positioning at least a first and second electrode in the heart;
  delivering an electrical stimulus from a stimulation system to said first electrode;
  sensing at both the first and second electrodes for a response by the heart to the electrical stimulus, wherein a capture of the heart by the electrical stimulus is confirmed if depolarization in excess of a predetermined threshold is sensed at the second electrode but depolarization is not sensed at the first electrode during a predetermined detection interval and non-capture is confirmed if depolarization in excess of the predetermined threshold is sensed at the first electrode or no depolarization is sensed at the second electrode during the predetermined detection interval; and
  increasing an amplitude of the electrical stimulus if capture of the heart by the electrical stimulus of the heart is not confirmed.

33. The method as recited in claim 32, further including the step of excluding sensing of stimulus artifacts.

34. The method of claim 32 and further including a step of setting the predetermined detection interval to a fixed value in patients having a non-functioning AV node and setting the predetermined detection interval to a function of a difference between an average of the patient's intrinsic AV interval over a predetermined number of intrinsic beats and an AV delay value programmed into the stimulation system in patients having a functioning AV node.

35. The method of claim 32 wherein the predetermined threshold is set as a multiple of an average of measured derivative of electrogram signals during the predetermined detection interval over a predetermined number of paced beats in patients with non-functioning AV nodes.

36. The method of claim 32 wherein the predetermined threshold is set as a fraction of an average of measured peak derivative signals of intrinsic depolarizations over a predetermined number of intrinsic beats in patients with functioning AV nodes.

37. A method of verifying capture of a patient's heart by an electrical stimulus delivered to the ventricles of the heart, comprising the steps of:
  (a) positioning a first electrode proximate a left ventricle, a second electrode proximate a right ventricle and a reference electrode within the patient;
  (b) delivering an electrical stimulus simultaneously to the first and second electrodes; and
  (c) sensing at both the first and second electrodes and the reference electrode for a response by the heart to the electrical stimulus wherein capture of the heart by the electrical stimulus is confirmed if depolarization is sensed at the reference electrode and not at the first and second electrodes during a predetermined detection interval, and non-capture is confirmed if no depolarization is sensed at the reference electrode or depolarization is sensed at either of the first and second electrode during the predetermined detection interval.

38. The method as in claim 37 and further including the step of increasing the amplitude of the electrical stimulus if capture is not confirmed.

39. A method of verifying capture of a patient's heart by an electrical stimulus delivered the heart comprising the steps of:
  (a) providing stimulus simultaneously to both right and left ventricle;
  (b) providing sensing circuits active during a detection window following delivery of a pacing pulse for sensing intrinsic and evoked ventricular depolarizations and detecting propagated depolarizations, the cardiac stimulation system further incorporating an autocapture algorithm for controlling the amplitude of delivered pacing pulses;
  (c) testing for presence of propagated depolarizations at either of the left ventricular electrode and the right ventricular electrode or absence of an evoked depolarization at both left and right ventricular electrodes during a predetermined detection window to establish lack of capture; and
  (d) testing for absence of propagated depolarization at both the left ventricular electrode and the right ventricular electrode and presence of evoked ventricular depolarization at any of the left and right ventricular electrodes to establish capture.

* * * * *